United States Patent [19]

Laghi

[11] Patent Number: 5,117,822
[45] Date of Patent: Jun. 2, 1992

[54] SILICONE HEART SPOON

[76] Inventor: Aldo A. Laghi, 13 Meridian La., Ballston LK, N.Y.

[21] Appl. No.: 680,958

[22] Filed: Apr. 5, 1991

[51] Int. Cl.⁵ .............................................. A61F 7/12
[52] U.S. Cl. .................................. 128/400; 128/401; 604/27; 604/30; 604/43; 604/113; 606/21
[58] Field of Search ............. 128/399, 400, 401, 24.1, 128/DIG. 21, DIG. 27, 850, 402, 403; 604/291, 27, 35, 328, 356, 268, 317, 43, 31–34, 45, 73, 113, 264; 606/21, 22, 23

[56] References Cited

U.S. PATENT DOCUMENTS

| | | | |
|---|---|---|---|
| 1,952,659 | 3/1934 | Dorrance | 604/291 |
| 3,133,539 | 5/1964 | Eidus | 128/403 |
| 4,259,961 | 4/1981 | Hood, III | 128/400 |
| 4,291,685 | 9/1981 | Taelman | 128/399 |
| 4,327,233 | 5/1982 | Gaille | 128/400 |
| 4,416,281 | 11/1983 | Cooper et al. | 128/400 |
| 5,014,695 | 5/1991 | Benak | 128/400 |
| 5,034,006 | 7/1991 | Hosoda et al. | 128/400 |

FOREIGN PATENT DOCUMENTS

| | | | |
|---|---|---|---|
| 164063 | 2/1949 | Australia | 128/400 |
| 1448068 | 9/1976 | United Kingdom | 128/400 |

*Primary Examiner*—Edward M. Coven
*Assistant Examiner*—Mark S. Graham
*Attorney, Agent, or Firm*—Joseph C. Mason, Jr.; Ronald E. Smith

[57] ABSTRACT

A tool that lowers the temperature of the heart during surgery or other times when blood flow to the heart is cut off. The tool has the appearance of a spoon and includes an elongate handle part and a heart-cradling part at the end of the handle. A first passageway formed in the handle delivers a continuous flow of cold liquid to the rim of the heart-cradling part of the tool and the cold liquid flows continuously out of perforations formed about the rim of that part of the tool for as long as refrigeration is needed. The tool is made of an uninsulated material so that the heart is cooled as the cold liquid flows out of the perforations and manifold is connected to the bottom wall of the heart-cradling part of the spoon and those apertures are in fluid communication, through a second passageway formed in the handle, with a source of negative pressure so that cold liquid that collects in the thoracic cavity below the heart of a supine patient is removed by connecting the second passageway to the source of negative pressure.

7 Claims, 3 Drawing Sheets

SILICONE HEART SPOON

TECHNICAL FIELD

This invention relates, generally, to tools having utility to the medical profession. More particularly, it relates to a surgical tool used to refrigerate cardiac muscle during time periods where flow of blood to the heart is interrupted.

BACKGROUND ART

To prepare a patient for open heart surgery, blood flowing to the patient's heart is diverted to a heart and lung machine that mechanically performs the functions of the heart and lungs during the surgical procedure. Thus deprived of its usual supply of oxygenated blood, heart muscle begins to deteriorate. Accordingly, recognizing the preservative effects of refrigeration, physicians began the practice of placing ice packs around the heart during surgery. The use of ice packs does produce some beneficial effect, but such use is somewhat unsatisfactory due to the physical limitations of ice packs. More particularly, they can not be positioned easily under the heart of a supine patient, they do not contact all of the walls of the heart and thus create warm pockets where muscle deterioration is not adequately curtailed, and they melt and require replacement which interferes with the physician's work. Moreover, the melted ice collects in a puddle below the heart, in the thoracic cavity, thereby affecting the lungs and possibly precipitating the onset of pulmonary problems or other complications; even the removal of such puddles during surgery creates an additional set of problems. Ice packs are also bulky and thus limit the surgeon's freedom of movement. Perhaps even more significantly, the ice packs cool everything with which they come into contact, i.e., they cool the thoracic cavity and thus the body in general, i.e., the cooling effect provided by ice packs is not localized. Surgical personnel who have worked with ice packs during surgery could point out even more drawbacks.

The heart of a supine patient is supported primarily by the walls of the thoracic cavity, and such walls are at normal body temperature. Thus, the very place where ice packs are least effective is the very place where heart cooling is most needed. There is a need, therefore, for a device that can be easily slipped under the heart of a supine patient to isolate the heart from the walls of the thoracic cavity. There is a need, further, for a device that cools the heart evenly, i.e., in the absence of pockets of uncooled areas. Moreover, there is a need for a device that removes any puddles of coolant that may collect in the thoracic cavity if such puddles become too large and threaten to overly cool said cavity and hence the patient's lungs. The needed device should be easy to manipulate and easy to operate as well.

A number of inventors have tried to develop the needed device, and some of the resulting surgical tools represent improvements over the ice pack method.

For example, U.S. Pat. No. 4,259,961 to Hood shows a plastic cooling is placed under the heart, but the device is structurally complex and difficult to maneuver during surgery. Additional U.S. patents of interest, all of which, like Hood, advanced the art to which they pertained, include U.S. Pat. Nos. 4,154,245 to Daily, 4,971,056 to Seacord, 4,416,281 to Cooper et. al., and 4,327,733 to Gallie. British patent 2,040,169, may also be of interest.

When the respective disclosures of these patents and many others are studied, together with the vast non-patent literature on the subject of heart refrigeration or myocardial hypothermia during surgery, those of ordinary skill in the industry that supplies tools to the medical profession are left with the firm conviction that the art has reached its highest level of development and that further significant progress in this field is unlikely.

DISCLOSURE OF INVENTION

A spoon-like device that slips easily under the heart of a supine patient has an elongate handle that facilitates its manipulation during surgery. The distal end of the device cradles the patient's heart and evenly cools all contacted areas thereof, plus contiguous areas. Two elongate bores or passageways are formed in the handle but said passageways are not directly interconnected to one another. A first passageway or inlet extends from the proximal end of the handle and encircles the rim of the heart-cradling part of the device. Multiple perforations are formed in that part of the first passageway that circumscribes the rim, and chilled saline solution, or other suitable chilled solution, pumped into the first passageway thus flows out of the perforations and cools the heart. Some of the solution may flow directly onto the heart and downwardly to the bottom of the heart-cradling means, but since the heart conforms to the shape of the cradling means and substantially fully occupies it, such flow is nominal. Most of the chilled saline flows downwardly on the outside of the cradling means, but the tool is made of a material having a high heat transfer coefficient, i.e., a non-insulating material so that the temperature-lowering quality of the chilled saline solution acts to refrigerate heart muscle as desired. Accordingly, a puddle of saline solution forms in the thoracic cavity in the vicinity of the heart-cradling part of the spoon. The novel device includes means for eliminating the puddle entirely if desired or regulating the size of the puddle to any desired volume. Specifically, the underside of the cradling means includes a downwardly projecting manifold having plural apertures formed therein along its extent, and those apertures are in fluid communication with a second passageway means that is formed in the handle of the spoon as mentioned earlier. The second passageway or outlet is in fluid communication with a source of negative pressure, and means are provided to regulate the amount of suction applied to the apertures. In this way, saline solution collected in a puddle in the thoracic cavity is aspirated into the second passageway and thus removed at any desired rate. Importantly, the first and second passageways are individually formed as aforesaid, thereby ensuring that short circuiting cannot occur, i.e., the saline solution cannot flow from the first passageway into the second in a way that bypasses the heart-cradling part of the spoon.

The structural simplicity of the device provides minimum interference with the surgeon's activities, and its elongate handle eases the task of surgical assistants.

Silicone is the preferred material from which the device is made, for several reasons. For example, silicone is inert, i.e., non-reactive to the human body. Moreover, since silicone is easily molded, the device can be mass produced at low unit cost. The flexibility of silicone also allows the heart-cradling part of the device to conform to the shape of the thoracic cavity.

It is therefore understood that a general but important object of this invention is to materially advance the art of tools that refrigerate heart tissue during surgery.

Another important object is to provide a tool that provides a localized cooling effect so that areas of the body that do not require cooling are substantially unaffected when the heart is refrigerated.

Still further objects are to provide a tool that is easy to manipulate so that it can be moved from one area to another, that does not interfere with the surgeon's freedom of movement, and that conforms to the shape of the thoracic cavity.

These and additional objects, features and advantages of the invention will become apparent as this description proceeds.

The invention accordingly comprises the features of construction, combination of elements, and arrangement of parts that will be exemplified in the construction hereinafter set forth and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

BEST MODES FOR CARRYING OUT THE INVENTION

Figure 1:
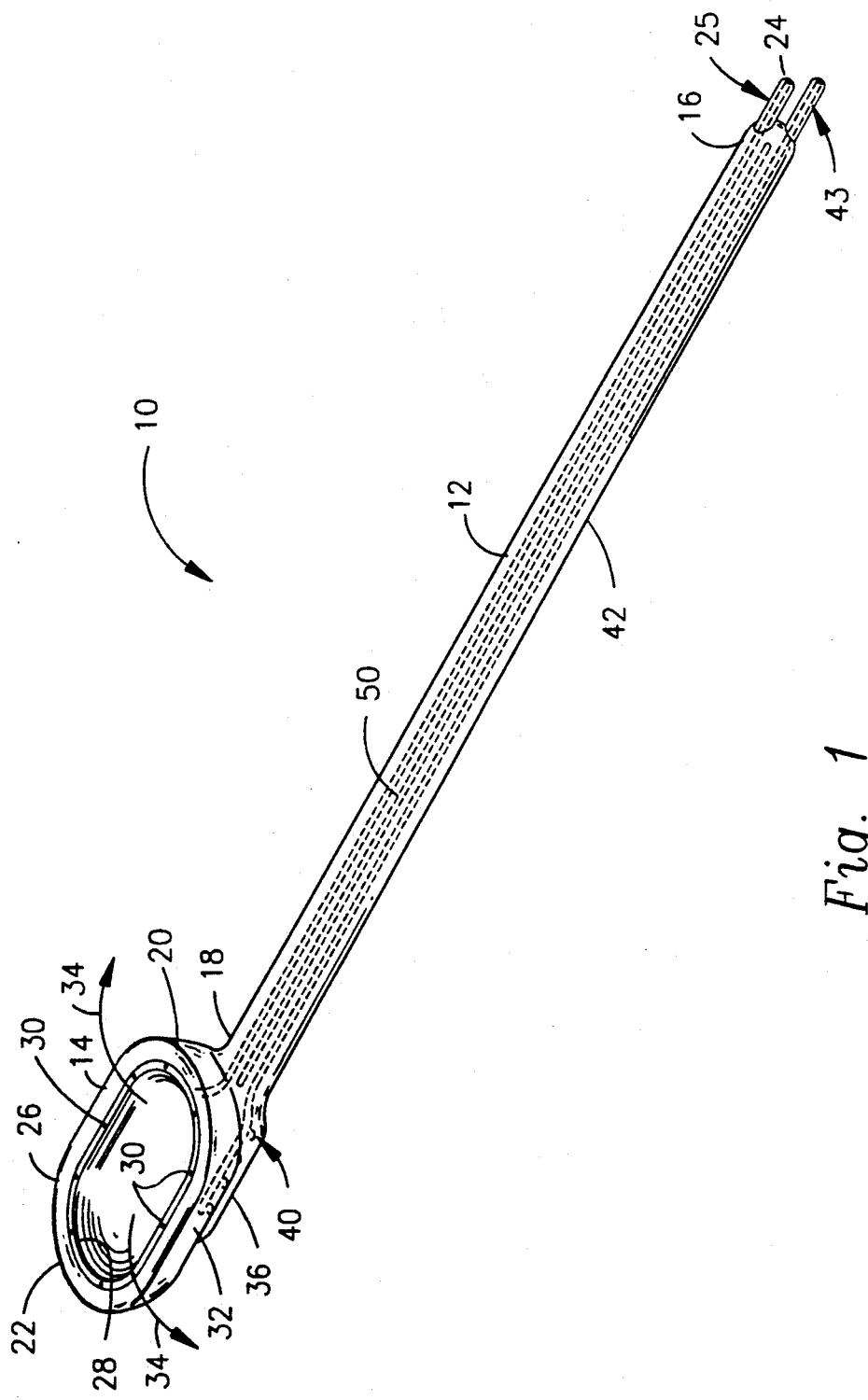
FIG. 1 is a perspective view of the novel heart spoon.

Referring now to FIG. 1, it will there be seen that an exemplary embodiment of the invention is denoted as a whole by the reference numeral 10.

Heart spoon 10 includes elongate handle 12 and heart-cradling part 14 integral therewith. The proximal end of the handle is denoted 16 and the distal end thereof is denoted 18. The proximal end of the heart-cradling part 14 is denoted 20 and the distal end of said part is denoted 22.

Cradling part 14 has an oblong configuration to conform to the shape of a human heart; it serves to cradle a heart under which it is inserted and to thereby separate the heart from physical contact with the walls of the thoracic cavity.

Figure 2:
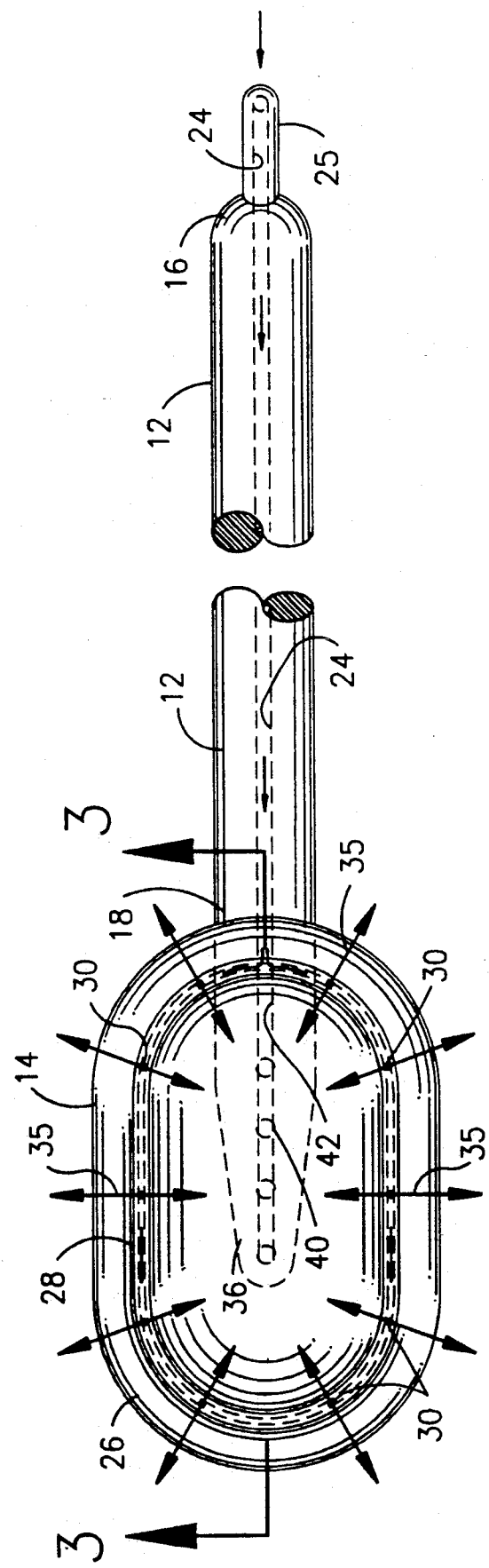
FIG. 2 is a top plan view thereof.
Figure 3:
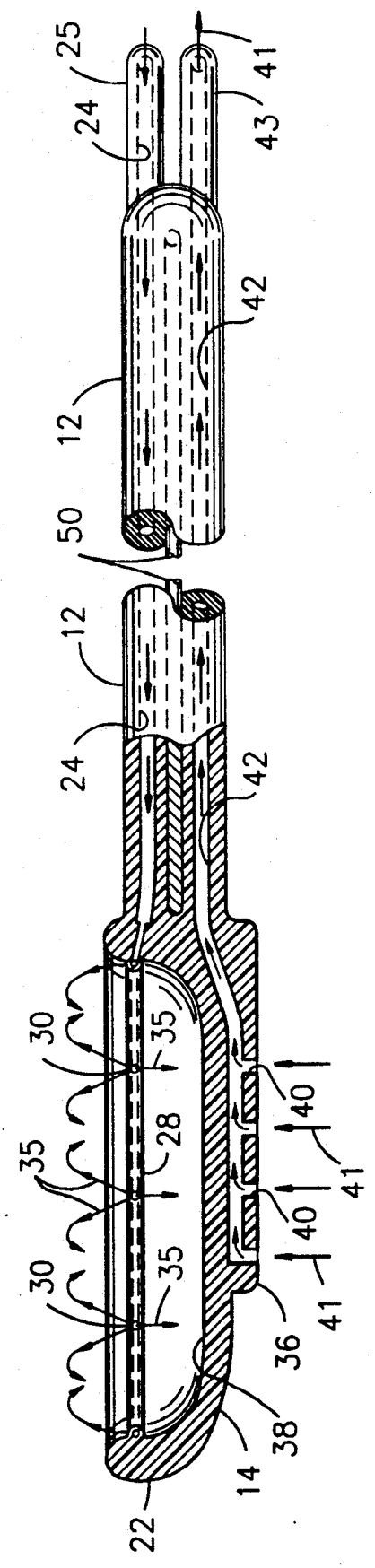
FIG. 3 is a partial sectional view taken along line 3—3 in FIG. 2.

As perhaps best shown in FIGS. 2 and 3, first or inlet passageway 24 is formed in handle 12 and extends from proximal end 16 thereof to the distal end 18 thereof. Said passageway then continues around the rim 26 of cradling part 14 as depicted, i.e., looped passageway 28 and first passageway 24 are the same passageway but are separately identified to better explain the structural aspects of the invention.

Plural perforations, collectively denoted 30, are formed in looped passageway 28 at equidistantly spaced intervals along the extent thereof to evenly chill the heart. Accordingly, chilled saline solution pumped into first passageway 24 under pressure seeps from said perforations 30 and flows upwardly to the rim, over the rim, and downwardly along the external walls 32 (FIG. 1) of the cradling part 14 as indicated by directional arrows 34. A source of chilled saline solution is readily available in all well-equipped operating rooms; it should be understood that the temperature of the solution is under the control of the physician and that the solution flows through the spoon as long as is needed. Since silicone is heat-conductive, the heart is thereby chilled. Small amounts of chilled saline will seep onto the heart itself, as desired, and some small amount may also seep into the bottom of the heat-cradling part, thereby chilling the heart as desired, as indicated by directional arrows 35 in FIGS. 2 and 3.

However, most of the chilled saline solution will flow down the external walls of the heart-cradling part as aforesaid, and will collect in a puddle around the bottom of said part; this puddle of chilled saline solution, if maintained at an optimal volume, can beneficially chill the heart where chilling is most needed, i.e., where the warm thoracic cavity is nearest the heart. However, over-chilling is not desirable, because such might lead to pulmonary problems.

Therefore, the invention includes novel means for draining the puddle or regulating its volume. A manifold member 36 of linear configuration is formed integrally with the bottom wall 38 of part 14, as perhaps best shown in FIG. 3, in depending relation to said bottom wall 38. Plural apertures, collectively denoted 40, are formed in said manifold at equidistantly spaced intervals and said apertures are in fluid communication with second or outlet fluid passageway 42. Passageway 42 is in fluid communication with a source of negative pressure, not shown, through a cannula, not shown. Thus, by properly regulating the amount of vacuum within second passageway 42, the chilled saline solution in the puddle is aspirated from the thoracic cavity at a preselected rate, as indicated by directional arrows 41 in FIG. 3. A simple pinch clamp carried by the cannula may be employed to regulate the vacuum in passageway 42. A similar pinch clamp or other suitable valve means may also be used to regulate the flow rate of saline solution through a cannula in fluid communication with first passageway 24 and hence around loop 28 as well.

Inlet passageway 24 and outlet passageway 42 extend into extension conduits 25 and 43, respectively, formed at the proximal end 16 of the heart spoon 10. These extension conduits facilitate connection of the cannulas, not shown, to said passageways.

The reference numeral 50 indicates a stiffening rod embedded within handle member 12 that performs the function its name implies. In a preferred embodiment, rod 50 is of aluminum construction; it is easily bent to conform to the nooks and crannies of the thoracic cavity. Rod 50 provides a means for easy repositioning of the heart-cradling member 14 while the surgeon performs surgery.

This invention is clearly new and useful. Moreover, it was not obvious to those of ordinary skill in this art at the time it was made, in view of the prior art considered as a whole in accordance with the requirements of law.

It will thus be seen that the objects set forth above, and those made apparent from the foregoing description, are efficiently attained and since certain changes can be made in the above description without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. A tool having utility in chilling a heart when blood flow to the heart is interrupted, comprising:
   an elongate handle member having a proximal end and a distal end;
   a heart-cradling means having a proximal end connected to the distal end of said handle member;
   a first passageway formed within said handle member, extending from the proximal end of the handle member to the distal end thereof;
   a looped passageway formed in said heart-cradling means about a rim part thereof, said looped passageway being in open fluid communication with said first passageway;
   a plurality of perforations formed in said looped passageway so that a liquid fluid flowing through said looped passageway seeps through said perforations;
   a manifold member connected to a bottom side of said heart-cradling means in depending relation thereto;
   a second passageway formed within said handle member, extending from said proximal end of said handle member to said distal end thereof;
   at least one aperture formed in said manifold member, and said at least one aperture being in open fluid communication with said second passageway;
   whereby said first passageway is adapted to be connected to a source of chilled liquid fluid under pressure to deliver said chilled fluid in a continuous flow to said looped passageway and hence to a heart cradled by said heart-cradling means; and
   whereby said second passageway is adapted to be connected to a source of negative pressure for aspirating liquid fluid collected in a puddle in the vicinity of said heart-cradling means into said second passageway means through said at least one aperture.

2. The tool of claim 1, wherein said manifold member has a linear configuration and wherein said at least one aperture formed therein includes a plurality of apertures formed in said manifold member along the extent thereof.

3. The tool of claim 2, wherein said plurality of perforations are equidistantly spaced about the periphery of said rim and adapted to provide even refrigeration of said heart.

4. The tool of claim 3, wherein said tool is made of silicone.

5. The tool of claim 4, further comprising a stiffening rod member embedded within said handle member to facilitate manipulation of the tool.

6. The tool of claim 5, wherein said stiffening rod member is formed of aluminum.

7. The tool of claim 6, further comprising valve means for regulating the flow of liquid fluid through said first and second passageways.

* * * * *